United States Patent [19]
Feldman et al.

[11] Patent Number: 5,315,056
[45] Date of Patent: May 24, 1994

[54] CATALYST REGENERATION IN A DEHYDROGENATION PROCESS

[75] Inventors: Robert J. Feldman, Passaic; Joseph M. Dufallo, Randolph, both of N.J.; William A. Schwartz, Fogelsville, Pa.; Theodore S. Williams, Middletown, N.J.

[73] Assignee: ABB Lummus Crest Inc., Bloomfield, N.J.

[21] Appl. No.: 837,027

[22] Filed: Feb. 14, 1992

[51] Int. Cl.⁵ .................. C07C 5/333; B01J 23/92; B01J 38/20; B01J 38/04
[52] U.S. Cl. .................. 585/659; 502/34; 502/38; 502/49; 502/53; 585/628; 585/634; 585/654; 585/662; 585/910
[58] Field of Search .................. 502/49, 56, 38, 34, 502/52; 585/634, 654, 659, 662, 910, 911

[56] References Cited

U.S. PATENT DOCUMENTS

| | | | |
|---|---|---|---|
| 2,330,462 | 9/1943 | Weiland | 502/52 |
| 2,391,327 | 12/1945 | Mekler | 502/52 |
| 2,461,838 | 2/1949 | Neuhart | 502/52 |
| 3,926,127 | 6/1976 | Woerner | 502/49 |
| 5,002,915 | 3/1991 | Harandi et al. | 502/38 |

*Primary Examiner*—Paul E. Konopka
*Attorney, Agent, or Firm*—Elliot M. Olstein; Raymond J. Lillie

[57] ABSTRACT

In a dehydrogenation process wherein catalyst is regenerated off-stream by use of heated air, at least two reactors are in the regeneration cycle, with regeneration air being heated to regeneration catalyst temperature for introduction into the first reactor, and thereafter being reheated to catalyst regeneration temperature and introduced into the second reactor. Such air may also be employed for preheating feed to the dehydrogenation reactor and/or for steam generation by heating such air to the temperature required for such procedure.

8 Claims, 2 Drawing Sheets

FIG. I

CATALYST REGENERATION IN A DEHYDROGENATION PROCESS

This invention relates to dehydrogenation and more particularly this invention relates to a dehydrogenation process wherein the dehydrogenation catalyst is periodically taken off-stream to effect regeneration thereof by contact with heated air.

In the dehydrogenation of feed by the use of a dehydrogenation catalyst, in many processes the dehydrogenation reactor is periodically taken off-stream for contact of the catalyst with heated air. Such off-stream contact of the catalyst with heated air serves the dual purpose of regenerating catalyst by removal of carbonaceous material and imparting heat to the catalyst for use in the endothermic on-stream dehydrogenation procedure.

As known in the art, a dehydrogenation reactor is taken off-stream and directly contacted with heated air for a period of time, and thereafter placed back on-stream. Thus, the dehydrogentation and catalyst regeneration procedure involves an on-stream dehydrogenation cycle for a period of time, followed by an off-stream regeneration cycle for a period of time, followed by an on-stream operation, etc.

The present invention is directed to improving the procedure for regeneration of the dehydrogenation catalyst in such a cyclic operation.

In accordance with an aspect of the present invention, there is provided an improvement in a dehydrogenation process wherein dehydrogenation reactors, containing dehydrogenation catalyst, are cycled between an on-stream dehydrogenation and off-stream catalyst regeneration by regenerating catalyst in at least two reactors off-stream in at least first and second portions of a catalyst regeneration cycle, with a first reactor being in a second stage of the regeneration cycle and a second reactor in a first stage of the regeneration cycle. Air heated to catalyst regeneration temperatures is used in the first catalyst regeneration and thereafter is heated to catalyst regeneration temperatures and used for regenerating catalyst in the second reactor. After the second portion of the regeneration cycle is completed, the first reactor is ready for use for on-stream dehydrogenation and after the first portion of the cycle is completed, the second reactor is moved to the second stage of the cycle.

The term "regeneration" as used herein encompasses adding heat to the catalyst for dehydrogenation and/or removal of foulants therefrom.

The air which is used for regenerating catalyst may also be heated and used in a heat exchanger to preheat feed to be introduced into an on-stream reactor, with such air after such preheating being reheated to catalyst regenerating temperatures prior to being introduced into an off-stream reactor which is in the catalyst regenerating recycle.

In general, the dehydrogenation catalyst is regenerated by heating the air to a temperature which is sufficient to reheat the catalyst to dehydrogenation temperatures while effecting some cleaning thereof. As the catalyst ages, the required temperature increases. In general, the air is heated to temperature of at least 1150° F. for newer catalyst and to higher temperatures for aged catalyst; for example, 1300° F. As should be apparent the maximum temperature is dictated by the catalyst sensitivity and reactor structural limitations.

The catalyst is generally regenerated at pressures sufficient to overcome the pressure drop of the system, with such pressures generally being from 0.9 to 1.3 atm gauge.

The quantity of air which is used for regenerating the catalyst is dependent upon the amount of heat which is to be imparted to the catalyst for use in the dehydrogenation reaction. In general, by proceeding in accordance with the present invention, wherein air is passed through at least two off-stream reactors, in series, air quantities are lower than those required in prior art procedures wherein regeneration air is used to reheat only a single reactor.

Although in many cases only two reactors are placed in series during off-stream regeneration whereby there are two portions to the regeneration cycle, it is possible to have three or more reactors in series, with the regeneration air contacting the reactors in reverse order to their place in the regeneration cycle, i.e., a reactor which is in a later portion of a regeneration cycle is contacted with the regenerating air, prior to a reactor which is in an earlier portion of the regeneration cycle.

The air is preferably heated to catalyst regeneration temperatures in a direct fired heater.

As hereinabove indicated, the regenerating air may be used to preheat hydrocarbon feed to the on stream dehydrogenation reactors. In such an embodiment, the air is heated to a temperature suitable for indirectly preheating the feed to dehydrogenation temperatures, with such heating of the air preferably being accomplished in a direct fired heater. In the embodiment where the dehydrogenation feed is preheated against regeneration air, the feed may be evaporated by indirect heat transfer against gaseous product from the dehydrogenation reactor, which reduces the refrigeration requirements for the product recovery; i.e., $C_3$ refrigeration duty for the low temperature product recovery unit can be reduced.

In still another embodiment, the regeneration air may also be employed to generate steam for the overall process. In such an embodiment, the air used for regenerating catalyst is heated to a temperature for generating steam (the air heating is preferably accomplished in a direct fired heater) and after steam generation the air is reheated to catalyst regenerating temperatures for direct contact with dehydrogenation catalyst in an off-stream reactor. Alternatively, the air is heated to steam generation temperatures for steam generation after being passed through all of the off-stream reactors in which the air is to be used for regenerating catalyst.

The invention will be further discribed with reference to the drawings wherein.

Figure 1:
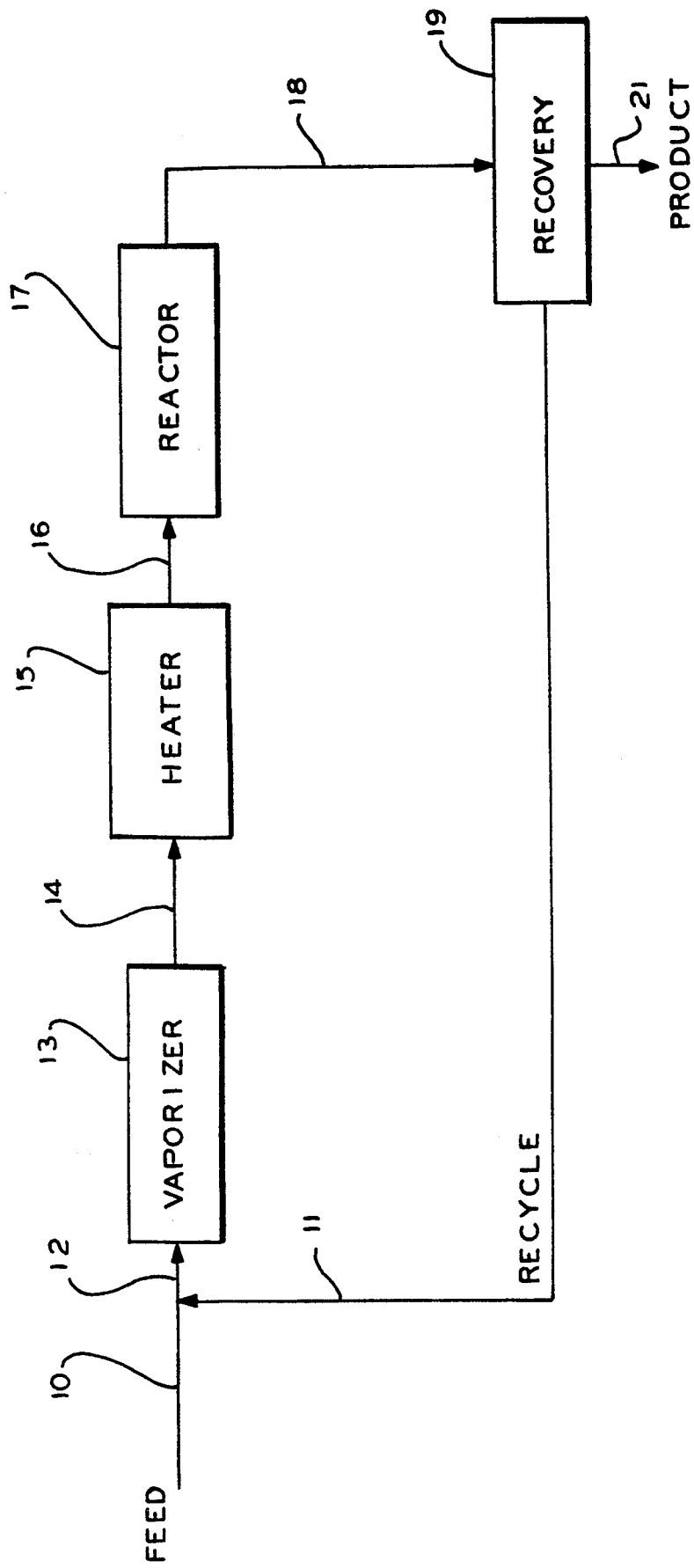
FIG. 1 is a simplified block diagram of on-stream dehydrogenation.

Referring now to the drawings, and in particular FIG. 1, which illustrates a simplified schematic block diagram of a dehydrogenation process for dehydrogenating, for example, an alkane, such as isobutane. It is to be understood, however, that the scope of the invention is not limited to such feed.

Fresh feed isobutane in line 10 is combined with recycle in line 11, and the combined feed is introduced into a vaporizer 13 wherein the liquid feed and recycle are vaporized. In general, the vaporized feed and recycle are withdrawn from vaporizer 13 through line 14 at a temperature of from about 35° to 40° F., with such vaporized feed being passed through a heater 15 wherein the combined feeds are heated to a temperature in the order of from about 1100° to 1200° F.

The preheated feed and recycle in line 16 are introduced into a dehydrogenation reactor 17, containing a suitable dehydrogenation catalyst such as, for example, a chromium oxide catalyst ($Cr_2O_3$). The catalyst, as known in the art, is generally admixed with inert particles, which inert particles function as heat carriers. In reactor 17, the isobutane is dehydrogenated to isobutene. In one embodiment, the dehydrogenation is effected as pressures below atmospheric pressures (generally in the order of from about 0.4 to about 0.6 atmosphere absolute) and at elevated temperatures, with the temperatures generally being in the order of from about 1050° to 1200° F. It is to be understood that in other embodiments, isobutane could be dehydrogenated at pressures above atmospheric pressure and at temperatures different than those hereinabove set forth.

Crude product is withdrawn from reactor 17 through line 18 and introduced into a separation and recovery section, schematically indicated as 19. Recycle is recovered for recycle through line 11, and product is recovered through line 21.

As known in the art, during the dehydrogenation, the dehydrogenation catalyst becomes contaminated, which requires regeneration of such catalyst. As known in the art, such regeneration of the catalyst is accomplished by taking a dehydrogenation reactor off-stream, and while the reactor is off-stream, the catalyst is regenerated by direct contact with heated air. In one embodiment, a dehydrogenation reactor remains on-stream for a period of from about 9 to about 10 minutes, and after such period, the reactor is taken off-stream for accomplishing regeneration of the dehydrogenation catalyst. During catalyst regeneration, a small amount of carbonaceous products are burned off the catalyst, and additional heat is added to the catalyst bed by the regeneration gas stream. The on-stream time is dependent upon the heat requirements for the dehydrogenation and the mass of catalyst and inerts used for the reactor. Since in a preferred embodiment, the catalyst mass provides a major portion of the dehydrogenation reaction heat, the reactor is taken off-stream as required to permit the catalyst to be reheated to provide such heat requirements. As should be apparent, the addition of external heat to the reactor can lengthen the on-stream time.

The present invention is directed to improving the overall process for producing dehydrogenated product by improving the procedure for regeneration of dehydrogenation catalyst.

Figure 2:
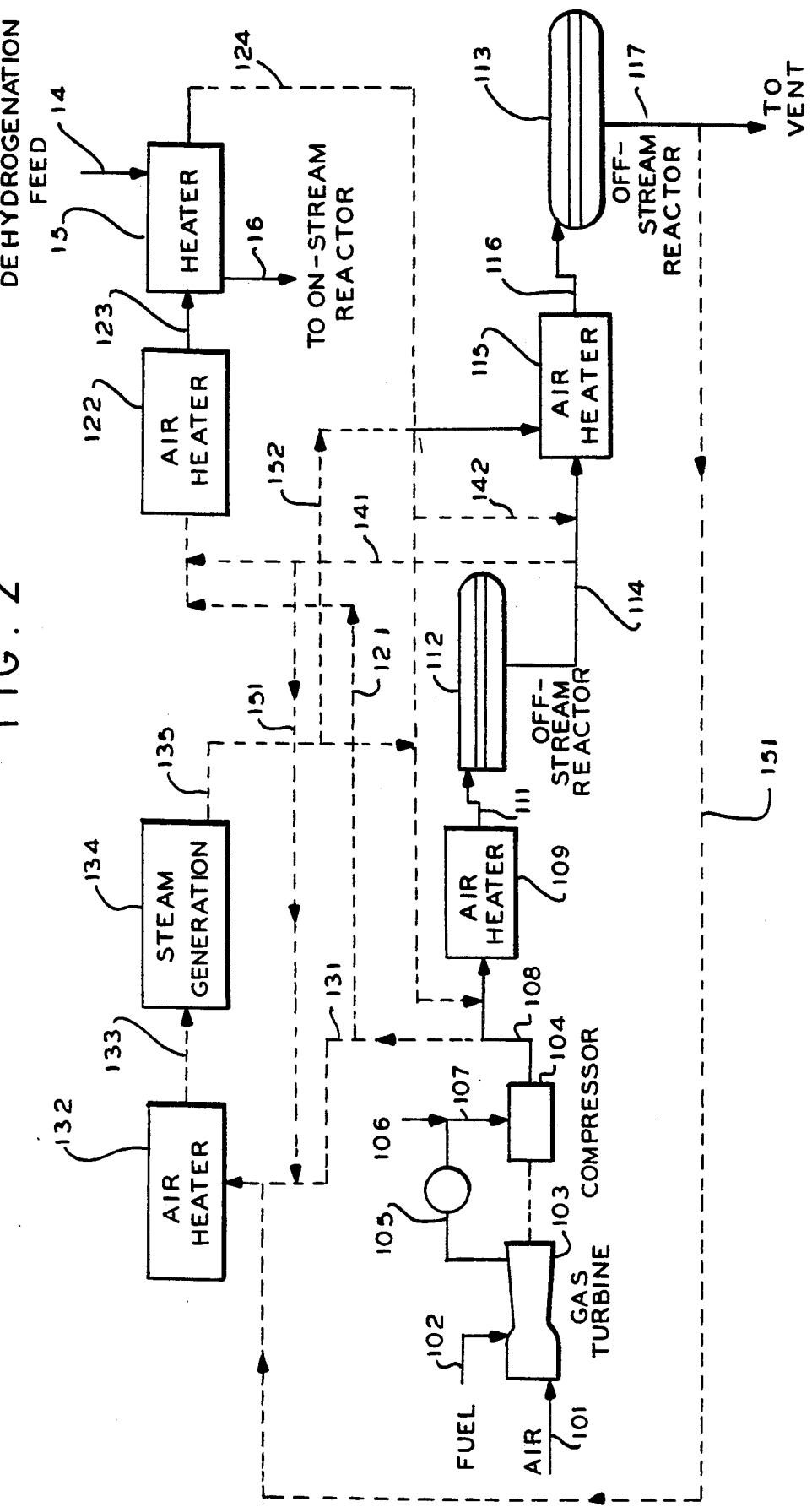
FIG. 2 is a simplified block diagram of off-stream catalyst regeneration.

The invention will be further described with reference to FIG. 2 which is a simplified schematic of an embodiment of catalyst regeneration in accordance with the present invention. In FIG. 2, the unbroken flow lines are illustrative of the air flow for regeneration of catalyst, with the broken flow lines being representative of alternative embodiments wherein the regeneration air is employed for preheating of feed and/or steam generation.

Referring now to FIG. 2 of the drawings, regeneration air in line 101, and fuel in line 102 are introduced into a gas turbine 103 which drives a compressor 104. The air withdrawn from turbine 103 through line 105 is combined with additional fresh air in line 106 and the combined stream is compressed in compressor 104 to pressures as hereinabove described. The compressed air in line 108 is then heated in an air heater 109 (which is preferably a direct fired heater) to a temperature which is suitable for effecting regeneration of dehydrogenation catalyst. Although a gas turbine has been particularly shown, other systems for compressing air can be used; e.g., a motor driven compressor.

In general, the air withdrawn from air heater 109 through line 111 is at a temperature of from about 1150° to about 1300° F., depending on the catalyst age. The air in line 111 is introduced into a first off-stream dehydrogenation reactor 112 which contains dehydrogenation catalyst to be regenerated.

In the embodiment of FIG. 2, the regeneration cycle is comprised of two portions, with reactor 112 being in the second and last portion of the regeneration cycle and reactor 113 being in the first portion of the regeneration cycle. In most cases, the total regeneration cycle for each reactor is from about 9 to about 12 minutes, with each portion of the regeneration cycle being of about equal time.

The heated air which is introduced into reactor 112 directly contacts the dehydrogenation catalyst therein, and as a result of such direct contact, the catalyst is regenerated by removing foulants, such as carbonaceous products. In addition, heat is imparted to the catalyst and inerts for providing dehydrogenation heat requirements.

Air is withdrawn from reactor 112 through line 114 (the temperature is generally about 1000° F. to 1075° F.), and such air is then introduced into an air-heater 115 to effect heating of the air to catalyst regeneration temperatures. The air heater 116 is also preferably a direct fired heater.

The heated air withdrawn from air heater 115 through line 116 is then introduced into reactor 113 to effect regeneration of dehydrogenation catalyst contained therein by direct contact between the air and catalyst.

Regeneration air is withdrawn from reactor 113 through line 117 for ultimate venting after any required treatment thereof.

After the required time period for the second portion of the regeneration cycle, which generally also is identical to the time period for the first portion of the regeneration cycle, the reactor 112 is ready for being placed on-stream for use in the dehydrogenation reaction, and the reactor 113 would be switched to the second portion of the regeneration cycle, with another dehydrogenation reactor, containing dehydrogenation catalyst to be regenerated, being placed in the first portion of the cycle. Thus, at such time, the inlet of reactor 113 would be connected to the outlet of heater 109, and the outlet of reactor 113 would be connected to the inlet of heater 115. Another dehydrogenation reactor, which would be taken off-stream, would have its inlet connected to the outlet of heater 115.

In a dehydrogenation plant for producing isobutylene in an amount of 320,000 metric tons per year, the air flow in a regenerator system as hereinabove described is preferably about 450,000 lbs/hr.

Thus, as should be apparent a dehydrogenation reactor passes through two portions of a regeneration cycle with the reactor in the first portion being regenerated by heated air which has previously been used for regenerating catalyst in a second portion of the regeneration cycle. After completion of the first portion of the regeneration cycle such reactor is moved to the second portion of the regeneration cycle for completion of catalyst regeneration.

Although the embodiment has been described with two portions of a regeneration cycle in which two reactors are simultaneously subjected to regeneration, as hereinabove indicated, it is possible to have three or more reactors in a regeneration cycle, with the regeneration air being passed through each of the reactors in inverse order to its position in the overall regeneration cycle, and with each reactor being moved through each portion of the regeneration cycle.

As hereinabove indicated, the regeneration air may also be employed for steam generation and/or preheating feed to the dehydrogenation reactor.

Thus, for example, referring to FIG. 2, the air from compressor 104 in line 108, instead of being directly introduced into air heater 109, may be passed through line 121 for introduction into the air heater 122, which is preferably a direct fired air heater. In air heater 122, the air is heated to a temperature suitable for preheating the feed to the dehydrogenation reactor 17 which is on-stream. The air from heater 122, in line 123 is then introduced into heater 15 wherein such air indirectly preheats dehydrogenation feed in line 14, with the preheated feed being withdrawn through line 16 for introduction into the on-stream dehydrogenation. The regeneration air withdrawn from heater 15 through line 124 may then be returned to air heater 109 for heating thereof as hereinabove described for use in regenerating catalyst in reactor 112. In such an embodiment, the feed may be vaporized in vaporizer 13 (FIG. 1) against crude product in the recovery system 19, which reduces refrigeration requirements.

As another alternative, the air from compressor 104 in line 108 may be passed through line 131 for introduction into an air heater 132, which is preferably a direct fired heater wherein the air is heated to a temperature suitable for steam generation. The heated air withdrawn from heater 132 in line 133 is then employed for generation of steam, schematically indicated as 134, with the air, after such steam generation, being passed through line 135 for return to air heater 109. Thus, as an alternative embodiment, the air in line 108, may be employed for generation of steam and/or preheating of feed prior to being employed for regenerating catalyst in an off-stream reactor in the second portion of the catalyst regeneration cycle.

As a further alternative, the air withdrawn from reactor 112, prior to being introduced into air heater 115 may be passed through line 141 for introduction into air heater 122 for effecting preheating of feed, as hereinabove described. After being used in such preheating, the air is returned to air heater 115, through line 142 for subsequent use in regenerating catalyst in reactor 113. As a further alternative, the air in line 114, prior to being introduced into air heater 115 may be passed through line 151 for introduction into air heater 132 for generating steam as hereinabove described. The air after being employed in such steam generation may be returned to air heater 115 through lines 135, 152 and 142 for regenerating catalyst in reactor 113, as hereinabove described.

As still a further alternative, the air removed from the last reactor 113 may be employed for generation of steam by passage through line 151 for introduction into air heater 132. After steam generation in system in 134, the air may be vented after any required treatment. Such an embodiment is less preferred in that carbonaceous deposits on the catalyst being regenerated in the initial portion of the regeneration cycle may deplete the oxygen content to a value at which subsequent heating of the air in a direct fired heater is not practical.

In still another embodiment, the catalyst may be regenerated by the use of a gas other than air. In such an embodiment, the catalyst regeneration imparts heat to the catalyst for the dehydrogenation reaction without cleaning thereof. The gas which is used may be an inert gas or a reducing gas. In such an embodiment the gas would be heated to regenerating temperatures by the use of indirect heat transfer, rather than a direct fired heater as described with reference to the drawings. In such an embodiment, a portion of the regeneration cycle could be accomplished by the use of air to clean and heat the catalyst, and another portion of the cycle could be accomplished with an inert or reducing gas to impart heat to the catalyst. For example, initially reactors 112 and 113 could be heated in series by air for a first time period and then reactors 112 and 113 could be heated in series by an inert or reducing gas for a second time period.

As another alternative, an entire off-stream cycle may be accomplished with an inert or reducing gas to impart heat and periodic cycles thereafter can use air when cleaning is also required.

The above modifications and others should be apparent to those skilled in the art from the teachings herein.

The air regeneration system of the present invention may be employed in a wide variety of procedures for dehydrogenation wherein regeneration of the dehydrogenation catalyst is required. The procedure is particularly applicable to the dehydrogenation of $C_2$, $C_3$ and $C_4$, & $C_5$ alkanes. As generally known in the art, such procedures employ a dehydrogenation catalyst such as a chromia-alumina catalyst, wherein the dehydrogenation is accomplished at temperatures in the order from about 1000° to about 1200° F. The dehydrogenation catalyst is preferably employed as a supported catalyst, and is preferably admixed with inerts which function as heat carriers. The heat imparted to the catalyst and inerts during the regeneration cycle furnishes all or part of the heat of reaction for the dehydrogenation.

Since the present invention is not directed to the dehydrogenation reaction per se, it is deemed that those of ordinary skill in the art would be able to accomplish dehydrogenation, in combination with the regeneration procedure of the present invention by reference to the known dehydrogenation procedures.

The present invention is particularly advantageous in that the air requirements for regeneration and heating of catalyst are reduced. In addition, there is improved fuel efficiency, and a lower oxygen content in the off-gas from the regeneration system.

Furthermore, when the embodiment of the present invention for utilizing the regeneration air for preheating of dehydrogenation feed is employed, there is a reduction in refrigeration requirements.

These and other advantageous should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. In a dehydrogenation process which employs a plurality of reactors each containing a dehydrogenation catalyst wherein the dehydrogenation catalyst requires periodic regeneration by contact with heated gas and wherein the reactors are cycled between use on-stream for dehydrogenation and use off-stream for regenerating catalyst, the improvement comprising:

regenerating catalyst off-stream in at least two reactors, the first of which is in a second portion of a catalyst regeneration cycle and the second of which is in a first portion of a catalyst regeneration cycle;

heating gas to a catalyst regeneration temperature and introducing such heated gas into the first reactor for heating and regenerating catalyst therein;

reheating gas obtained from the first reactor to a catalyst regeneration temperature and introducing such reheated gas into the second reactor for heating and regenerating catalyst therein; and after completion of the second portion regeneration cycle, removing the first reactor from the regeneration cycle for subsequent use on-stream and placing the second reactor in the second portion of the regeneration cycle.

2. The process of claim 1 wherein the gas is air.

3. The process of claim 2 wherein the air is initially preheated to a temperature for preheating feed to an on-stream reactor and the preheated air is employed for preheating feed to an on-stream dehydrogenation reactor by indirect heat transfer, said preheating by air being effected prior to use thereof in the first reactor which is in the second portion of the regeneration cycle.

4. The process of claim 2 wherein air after being employed for regeneration of catalyst in the first reactor is heated to a temperature for steam generation and said heated air is employed for generating steam by indirect heat transfer, said steam generation being effected prior to use of the air in the second reactor.

5. The process of claim 2 wherein the air is heated and reheated in direct fired heaters.

6. The process of claim 2 wherein the catalyst is a chromium oxide catalyst.

7. The process of claim 2 wherein the air temperature after regeneration in each of the reactors is a temperature of from 1000° F. to 1075° F.

8. The process of claim 2 wherein the air prior to being introduced into each of the first and second reactor is heated to a temperature of from about 1150° F. to 1300° F.

* * * * *